US00PP34004P2

(12) United States Plant Patent
Barnes

(10) Patent No.: US PP34,004 P2
(45) Date of Patent: Mar. 8, 2022

(54) ***HELIOTROPIUM* PLANT NAMED 'WNHPAULAV'**

(50) Latin Name: *Heliotropium hybrida*
Varietal Denomination: WNHPAULAV

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 17/371,466

(22) Filed: Jul. 9, 2021

(51) Int. Cl.
*A01H 5/02* (2018.01)
*A01H 6/00* (2018.01)

(52) U.S. Cl.
USPC ..... Plt./438

(58) Field of Classification Search
USPC ..... Plt./438
CPC ..... A01H 5/02; A01H 5/00; A01H 6/00
See application file for complete search history.

*Primary Examiner* — June Hwu
(74) *Attorney, Agent, or Firm* — C. Anne Whealy

(57) ABSTRACT

A new and distinct cultivar of *Heliotropium* plant named 'WNHPAULAV', characterized by its upright to somewhat outwardly spreading and mounding plant habit; vigorous growth habit and rapid growth rate; freely branching habit; dense and bushy plant form; freely flowering habit; relatively large inflorescences; fragrant purple-colored flowers with bright yellow-colored throats; and good garden performance.

2 Drawing Sheets

Figure 1:
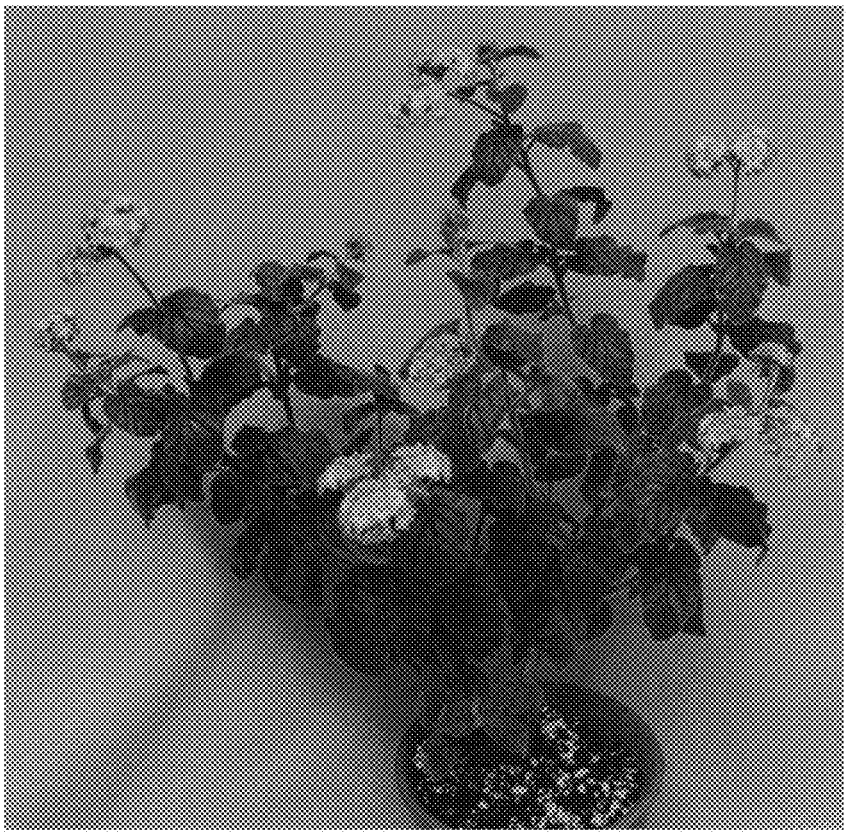

Botanical designation: *Heliotropium hybrida.*
Cultivar denomination: 'WNHPAULAV'.

BACKGROUND OF THE INVENTION

The present invention relates to a new and distinct cultivar of *Heliotropium* plant, botanically known as *Heliotropium hybrida,* commonly referred to as Heliotrope and hereinafter referred to by the name 'WNHPAULAV'.

The new *Heliotropium* plant is a product of a planned breeding program conducted by the Inventor in Bonsall, Calif. The objective of the breeding program is to create new upright, freely-branching and freely-flowering *Heliotropium* plants with attractive leaves and flowers and good garden performance.

The new *Heliotropium* plant originated from an open-pollination in June, 2018 of a proprietary selection of *Heliotropium hybrida* identified as code number 16BR048, not patented, as the female, or seed, parent with an unknown selection of *Heliotropium hybrida* as the male, or pollen, parent. The new *Heliotropium* plant was discovered and selected by the Inventor as a single flowering plant from within the progeny of the stated open-pollination in a controlled greenhouse environment in Bonsall, Calif. on Aug. 2, 2018.

Asexual reproduction of the new *Heliotropium* plant by vegetative terminal cuttings in Bonsall, Calif., since Aug. 7, 2018 has shown that the unique features of this new *Heliotropium* plant are stable and reproduced true to type in successive generations.

SUMMARY OF THE INVENTION

Plants of the new *Heliotropium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNHPAULAV'. These characteristics in combination distinguish 'WNHPAULAV' as a new and distinct *Heliotropium* plant:

1. Upright to somewhat outwardly spreading and mounding plant habit.
2. Vigorous growth habit and rapid growth rate.
3. Freely branching habit; dense and bushy plant form.
4. Freely flowering habit.
5. Relatively large inflorescences.
6. Fragrant purple-colored flowers with bright yellow-colored throats.
7. Good garden performance.

Plants of the new *Heliotropium* can be compared to plants of the female parent selection. Plants of the new *Heliotropium* differ primarily from plants of the female parent selection in the following characteristics:

1. Plants of the new *Heliotropium* are more upright than and not as outwardly spreading as plants of the female parent selection.
2. Plants of the new *Heliotropium* have larger flowers than plants of the female parent selection.

Plants of the new *Heliotropium* can be compared to plants of *Heliotropium amplexicaule* X *Heliotropium leiocarpum* 'USHTRPO303', disclosed in U.S. Plant Pat. No. 21,681. In side-by-side comparisons, plants of the new *Heliotropium* differ from plants of 'USHTRPO303' in the following characteristics:

1. Plants of the new *Heliotropium* are more upright than and not as outwardly spreading as plants of 'USHTRPO303'.
2. Plants of the new *Heliotropium* have stronger and sturdier lateral branches than plants of 'USHTRPO303'.

3. Plants of the new *Heliotropium* have larger flowers than plants of 'USHTRPO303'.

Plants of the new *Heliotropium* can also be compared to plants of *Heliotropium arborescens* 'Atlanta', disclosed in U.S. Plant Pat. No. 11,326. In side-by-side comparisons, plants of the new *Heliotropium* differ from plants of 'Atlanta' in the following characteristics:

1. Plants of the new *Heliotropium* have smaller inflorescences than plants of 'Atlanta'.
2. Plants of the new *Heliotropium* have larger flowers than plants of 'Atlanta'.
3. Plants of the new *Heliotropium* have purple-colored flowers with bright yellow-colored throats whereas plants of 'Atlanta' have violet-colored flowers with white-colored throats.

BRIEF DESCRIPTION OF THE PHOTOGRAPHS

The accompanying colored photographs illustrate the overall appearance of the new *Heliotropium* plant showing the colors as true as it is reasonably possible to obtain in colored reproductions of this type. Colors in the photographs may differ slightly from the color values cited in the detailed botanical description which accurately describe the colors of the new *Heliotropium* plant.

The photograph on the first sheet (FIG. 1) is a side perspective view of a typical flowering plant of 'WNHPAULAV' grown in a container.

Figure 2:
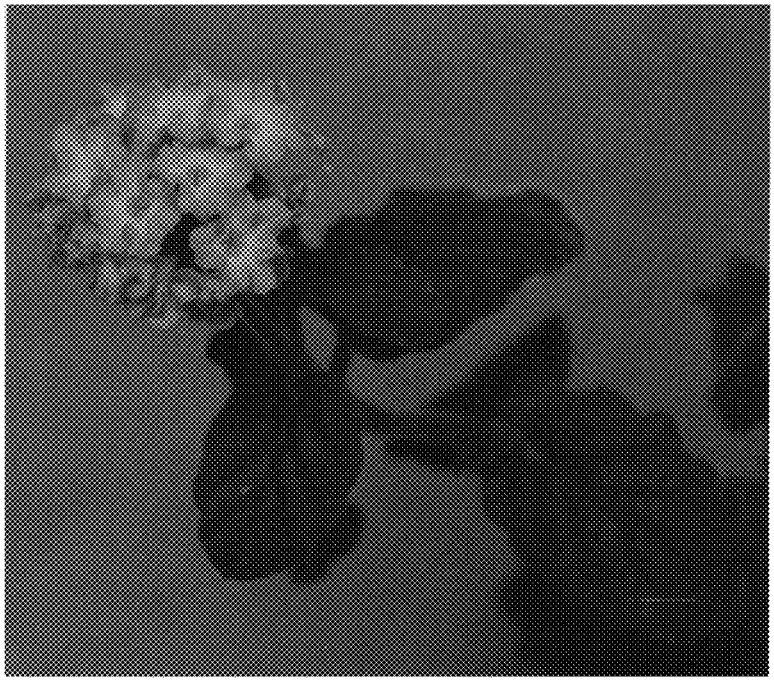

The photograph on the second sheet (FIG. 2) is a close-up view of a typical flowering plant of 'WNHPAULAV'.

DETAILED BOTANICAL DESCRIPTION

The aforementioned photographs and following observations and measurements describe plants grown during the late summer and early autumn in 10.8-cm containers in a corrugated polycarbonate-covered greenhouse in Carlton, Mich. and under cultural practices typical of commercial *Heliotropium* production. During the production of the plants, day temperatures averaged 26° C., night temperatures averaged 20° C. and light levels averaged 9,290 footcandles. Plants were pinched three weeks after planting and were ten weeks from planting rooted cuttings when the photographs and description were taken. In the following description, color references are made to The Royal Horticultural Society Colour Chart, 2015 Edition, except where general terms of ordinary dictionary significance are used.

Botanical classification: *Heliotropium hybrida* 'WNHPAULAV'.

Parentage:

*Female, or seed, parent.*—Proprietary selection of *Heliotropium hybrida* identified as code number 16BR048, not patented.

*Male, or pollen, parent.*—Unknown selection of *Heliotropium hybrida*, not patented.

Propagation:

*Type.*—By vegetative terminal cuttings.

*Time to initiate roots, summer.*—About five days at temperatures about 24° C. to 29° C.

*Time to initiate roots, winter.*—About eight days at temperatures about 18° C. to 22° C.

*Time to produce a rooted young plant from unrooted cuttings, summer.*—About 17 days at temperatures about 24° C. to 29° C.

*Time to produce a rooted young plant from unrooted cuttings, winter.*—About 21 days at temperatures about 18° C. to 22° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial typically grown as a container and garden plant; upright to somewhat outwardly spreading and mounding plant habit; vigorous growth habit and rapid growth rate.

*Branching habit.*—Freely basal branching with lateral branches potentially developing at every node; bushy and dense appearance.

*Plant height.*—About 32 cm.

*Plant width.*—About 28 cm by 39 cm.

*Lateral branch description.*—Length: About 19 cm. Diameter: About 5 mm. Internode length: About 3.5 cm to 4 cm. Strength: Strong, sturdy; flexible. Aspect: Mostly upright to about 20° from vertical; curving upright. Texture and luster: Densely pubescent; slightly glossy. Color, developing and developed: Close to 144A.

Leaf description:

*Arrangement.*—Opposite before flowering and alternate after flowering; simple.

*Length.*—About 5.2 cm.

*Width.*—About 3.3 cm.

*Shape.*—Narrowly ovate.

*Apex.*—Acute; curved downward with development.

*Base.*—Cordate.

*Margin.*—Entire, sinuate.

*Texture and luster, upper surface.*—Pubescent; slightly glossy.

*Texture and luster, lower surface.*—Mostly glabrous with pubescence along veins and margins; matte.

*Venation pattern.*—Pinnate.

*Color.*—Developing leaves, upper surface: Close to between 146A and 147A. Developing leaves, lower surface: Close to 146A. Fully expanded leaves, upper surface: Close to 147A; venation, close to 147A. Fully expanded leaves, lower surface: Close to 146A; venation, close to 146D.

*Petioles.*—Length: About 1.4 cm. Diameter: About 3 mm. Strength: Moderately strong; flexible. Texture and luster, upper and lower surfaces: Pubescent; slightly glossy. Color, upper surface: Close to 146A. Color, lower surface: Close to 146B to 146C.

Flower description:

*Flower arrangement and shape.*—Single actinomorphic funnelform flowers arranged on compact terminal helicoid cymes; three to four cymes per stem apex; freely flowering habit with about 15 to 20 flowers developing per inflorescence; flowers face mostly upright to outwardly to curling backwards depending on position on helicoid cymes; flowers sessile.

*Fragrance.*—Fragrant; pleasant.

*Natural flowering season.*—Early flowering habit, plants begin flowering about six to seven weeks after planting; plants flower from late spring until the autumn in Michigan.

*Flower longevity.*—Flowers last about three to five days on the plant; flowers persistent.

*Flower buds.*—Length: About 4 mm. Diameter: About 2 mm. Shape: Oblong. Texture and luster: Slightly pubescence; slightly glossy. Color: Distally, close to N82A and proximally, close to 144A.

*Inflorescence height.*—About 2 cm to 3 cm.

*Inflorescence diameter.*—About 2 cm to 3 cm.

*Flower diameter.*—About 1 cm.

*Flower length* (*depth*).—About 7.5 mm.

*Flower throat diameter.*—About 2 mm to 3 mm.

*Flower tube length.*—About 4 mm to 5 mm.

*Flower tube diameter, proximally.*—About 1 mm.

*Petals.*—Quantity and arrangement: Five petals fused in a single salverform whorl. Petal lobe length (from throat): About 5 mm. Petal lobe width: About 4 mm. Petal lobe shape: Broadly ovate. Petal lobe apex: Rounded to somewhat acute. Petal lobe margin: Finely crenate; ruffled and undulate. Petal lobe texture and luster, upper surface: Smooth, glabrous; velvety; matte. Petal lobe texture and luster, lower surface: Smooth, glabrous; matte. Throat texture and luster: Pubescent. Tube texture and luster: Smooth, glabrous. Color: When opening, upper surface: Close to N82A. When opening, lower surface: Close to N82B to N82C. Fully opened, upper surface: Close to N82B to N82C; towards the throat, close to NN155C; venation, similar to lamina colors; color becoming closer to N82D to eventually close to 85B to 85D with subsequent development. Fully opened, lower surface: Close to N82C to N82D; venation, close to N82C to N82D; color becoming closer to N82D to eventually close to 85B to 85D with subsequent development. Flower throat (inside): Close to 7A; venation, close to 7A. Flower tube (outside): Close to 7A to 7B; venation, close to 7A to 7B.

*Sepals.*—Quantity and arrangement: Five sepals fused in a single star-shaped whorl. Length: About 3 mm. Width: About 1 mm. Shape: Lanceolate. Apex: Acute. Margin: Entire. Texture, upper surface: Mostly glabrous with pubescence along margins. Texture, lower surface: Pubescent. Color: When opening and fully developed, upper surface: Close to 146A. When opening and fully developed, lower surface: Close to 146A.

*Peduncles.*—Length: About 1.5 cm to 2 cm. Width: About 2 mm. Strength: Strong; flexible. Angle: Upright to about 45° from lateral stem axis. Texture: Densely pubescent. Color: Close to 146A to 146B.

*Reproductive organs.*—Stamens: Quantity per flower: About five; adnate to the throat. Filament length: Less than 0.5 mm. Filament color: Close to 157A. Anther length: About 1 mm to 1.5 mm. Anther shape: Oblong. Anther color: Close to 79A. Pollen amount: Scarce. Pollen color: Close to 158C. Pistils: To date, pistil development has not been observed on plants of the new *Heliotropium.*

*Seeds and fruits.*—To date, seed and fruit production has not been observed on plants of the new *Heliotropium* plant.

Pathogen & pest resistance: To date, plants of the new *Heliotropium* have not been noted to be resistant to pathogens and pests common to *Heliotropium* plants.

Garden performance: Plants of the new *Heliotropium* have exhibited good garden performance and to be tolerant to rain, wind and temperatures ranging from about 2° C. to about 35° C.

It is claimed:

1. A new and distinct *Heliotropium* plant named 'WNH-PAULAV' as illustrated and described.

* * * * *